(12) United States Patent
White et al.

(10) Patent No.: US 8,398,653 B2
(45) Date of Patent: Mar. 19, 2013

(54) SURGICAL METHOD UTILIZING A SOFT-TIPPED ANVIL

(75) Inventors: Nathan H. White, Palo Alto, CA (US); Michael P. Schaller, Palo Alto, CA (US); Luke W. Clauson, Redwood City, CA (US); Michael Murillo, Palo Alto, CA (US); Bernard A. Hausen, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 154 days.

(21) Appl. No.: 12/968,641

(22) Filed: Dec. 15, 2010

(65) Prior Publication Data

US 2011/0106150 A1 May 5, 2011

Related U.S. Application Data

(62) Division of application No. 11/859,058, filed on Sep. 21, 2007, now Pat. No. 7,866,523.

(51) Int. Cl.
*A61B 17/068* (2006.01)

(52) U.S. Cl. .......... 606/139; 606/153; 606/219; 227/19; 227/175.1; 227/176.1; 227/180.1

(58) Field of Classification Search .................. 227/19, 227/176.1, 175.1, 180.1, 61; 606/139, 151, 606/153, 219, 141, 148, 51, 213
See application file for complete search history.

(56) References Cited

U.S. PATENT DOCUMENTS

| | | | |
|---|---|---|---|
| 4,873,977 A | 10/1989 | Avant et al. | |
| 5,047,039 A | 9/1991 | Avant et al. | |
| 5,234,454 A | 8/1993 | Bangs | |
| 5,397,324 A * | 3/1995 | Carroll et al. | 606/139 |
| 5,522,788 A | 6/1996 | Kuzmak | |
| 5,527,298 A | 6/1996 | Vance et al. | |
| 5,527,322 A * | 6/1996 | Klein et al. | 606/144 |
| 5,766,187 A | 6/1998 | Sugarbaker | |
| 5,772,099 A | 6/1998 | Gravener | |
| 5,861,005 A | 1/1999 | Kontos | |
| 5,908,427 A | 6/1999 | McKean et al. | |
| 5,993,464 A * | 11/1999 | Knodel | 606/139 |
| 6,099,551 A | 8/2000 | Gabbay | |
| 6,248,117 B1 | 6/2001 | Blatter | |
| 6,551,334 B2 | 4/2003 | Blatter et al. | |
| 6,569,173 B1 | 5/2003 | Blatter et al. | |
| 6,616,661 B2 | 9/2003 | Wellman et al. | |
| 6,623,494 B1 | 9/2003 | Blatter | |
| 6,626,921 B2 | 9/2003 | Blatter et al. | |
| 6,652,542 B2 | 11/2003 | Blatter et al. | |
| 6,663,590 B2 | 12/2003 | Blatter | |
| 6,726,694 B2 | 4/2004 | Blatter et al. | |
| 6,736,825 B2 | 5/2004 | Blatter et al. | |

(Continued)

OTHER PUBLICATIONS

"510(k) Notification for the Cardica C-Port Anastomosis System", Section 9, "Substantial Equivalence," and Appendices B, C, E, (Unpublished).

*Primary Examiner* — Scott A. Smith
(74) *Attorney, Agent, or Firm* — Cardica, Inc.

(57) ABSTRACT

A surgical method for treating a tissue structure having a wall and a lumen may include providing a substantially rigid anvil and a flexible tip affixed to and extending from the distal end of that anvil; making an incision in the wall of the tissue structure; inserting the flexible tip and at least a portion of the rigid anvil through the incision into the lumen of the tissue structure; and deforming at least one connector, introduced from outside the wall of the tissue structure, against the portion of the rigid anvil located within the lumen of the tissue structure.

8 Claims, 2 Drawing Sheets

U.S. PATENT DOCUMENTS

| | | |
|---|---|---|
| 6,743,244 B2 | 6/2004 | Blatter et al. |
| 6,767,356 B2 | 7/2004 | Kanner et al. |
| 7,063,699 B2 | 6/2006 | Hess et al. |
| 7,300,444 B1 * | 11/2007 | Nielsen et al. ............ 606/153 |
| 7,866,523 B1 * | 1/2011 | White et al. ............ 227/175.1 |
| 7,914,543 B2 * | 3/2011 | Roth et al. ............ 606/153 |
| 8,136,711 B2 * | 3/2012 | Beardsley et al. ......... 227/175.1 |
| 2001/0004698 A1 | 6/2001 | Blatter et al. |
| 2001/0023354 A1 | 9/2001 | Blatter et al. |
| 2003/0014064 A1 | 1/2003 | Blatter |
| 2004/0097994 A1 | 5/2004 | Blatter et al. |
| 2004/0225306 A1 | 11/2004 | Blatter et al. |
| 2005/0216043 A1 | 9/2005 | Blatter et al. |
| 2006/0167485 A1 | 7/2006 | Blatter |

* cited by examiner

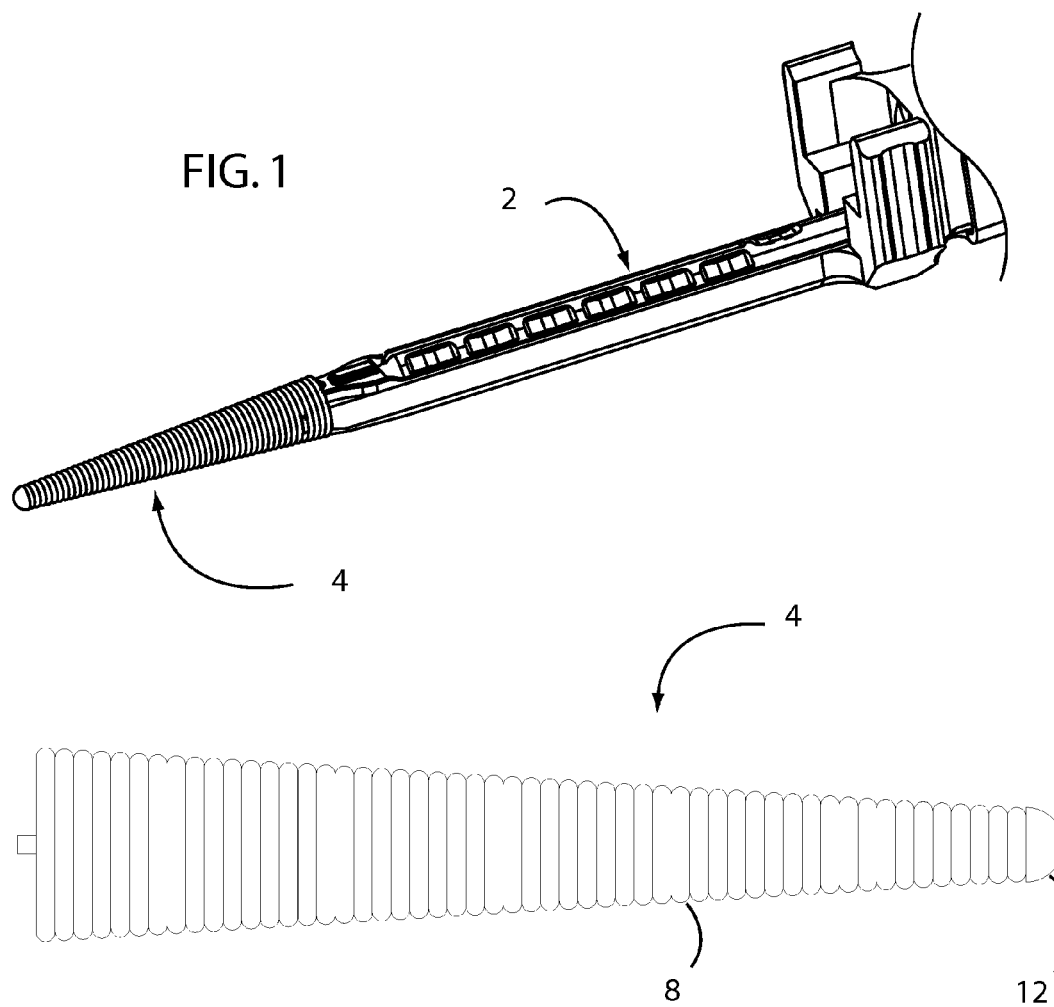
FIG. 1
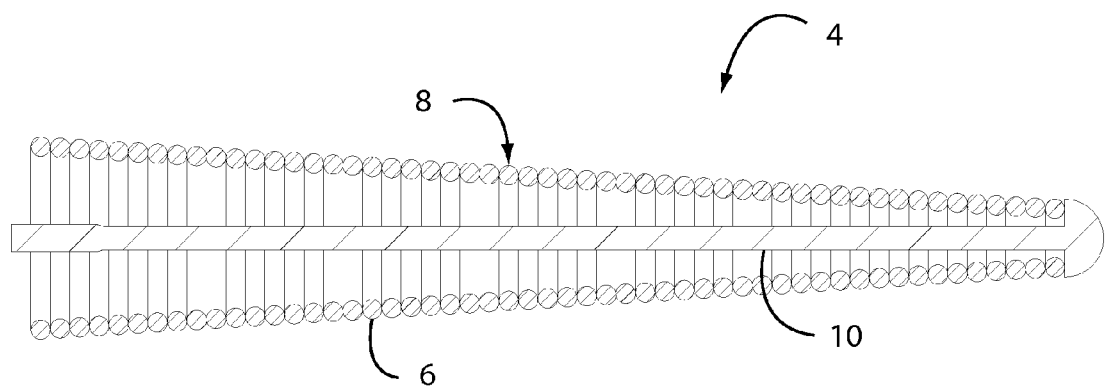
FIG. 2
FIG. 3

SURGICAL METHOD UTILIZING A SOFT-TIPPED ANVIL

This application is a divisional of U.S. patent application Ser. No. 11/859,058, filed on Sep. 21, 2007, now U.S. Pat. No. 7,866,523 which is hereby incorporated by reference in its entirety.

FIELD OF THE INVENTION

The invention generally relates to a surgical tool and method, and more specifically to a surgical tool having an anvil.

BACKGROUND

Surgical staplers, such as those used for vascular anastomosis, often include an anvil against which staples are deformed. As one example, U.S. patent application Ser. No. 11/054,265, filed on Feb. 9, 2005 (the "'265 application"), which is hereby incorporated by reference in its entirety, described an anastomosis stapler including a staple holder and an anvil, where that anvil is inserted through the wall of a target vessel at or in proximity to the anastomosis site. The distal end of that anvil is blunt, as is typical for such anvils, in order to prevent inadvertent damage to the back wall of the target vessel after the end of the anvil has been inserted through the wall of the target vessel. Before the anvil is inserted through the wall of the target vessel, a small incision is made in the wall of the target vessel with a scalpel. The target vessel may be a coronary artery. The anvil is then inserted through the incision in the wall of the target vessel into the lumen of the target vessel. Because the incision in the wall of the target vessel is small, it can be inconvenient to locate the incision with the end of the anvil and then insert the anvil through the incision. This inconvenience may be compounded when the target vessel is a coronary artery and the anvil is used during beating-heart surgery.

BRIEF DESCRIPTION OF THE DRAWINGS

FIG. 1 is a perspective view of an anvil with a flexible tip.
FIG. 2 is a side view of one example of a flexible tip.
FIG. 3 is a cross-section view of the flexible tip of FIG. 2.

The use of the same reference symbols in different figures indicates similar or identical items.

DETAILED DESCRIPTION

Figure 4:
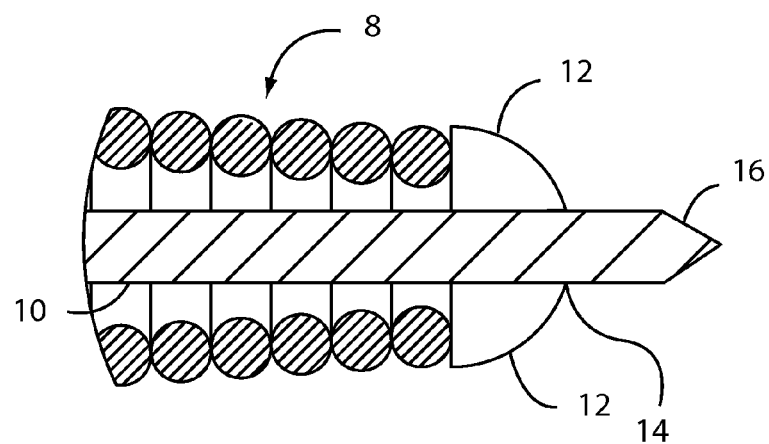
FIG. 4 is a cross-section view of another example of a flexible tip.

Referring to FIG. 1, an anvil 2 is shown. The anvil 2 may be configured substantially as described in the '265 application. Alternately, the anvil 2 may be configured in any other suitable manner. The anvil 2 may be rigid. One or more connectors (not shown) may be urged, driven or otherwise moved into contact with the anvil 2, thereby causing at least one of those connectors to deform, change state or otherwise alter its configuration. The connector or connectors used in conjunction with the anvil may be clips, staples or any other suitable connectors. As one example, the connectors may be as described in the '265 application. The anvil 2 may be pivotally connected to a connector holder (not shown), as described in the '265 application. That connector holder may hold one or more connectors.

A flexible tip 4 extends from the distal end of the anvil 2. The flexible tip 4 has an initial position relative to the anvil 2. The centerline of the flexible tip 4 when the flexible tip 4 is in the initial position is referred to as the initial centerline of the flexible tip 4. The flexible tip 4 is characterized as "flexible" because at least the distal end of the flexible tip 4 is deflectable away from the initial centerline of the flexible tip 4, by any suitable amount. The flexible tip 4 may be generally elastic, such that the flexible tip 4 returns generally to its initial position when external forces are removed from it. Alternately, the flexible tip 4 substantially does not store energy to return its initial position after being deflected away from it, and simply remains in any position in which it is placed until it is moved again.

At least the anvil 2 may be elongated, and the flexible tip 4 may be elongated as well. The flexible tip 4, and the anvil 2, may be oriented generally longitudinally. If so, the longitudinal centerlines of the flexible tip 4 and the anvil 2 may be substantially collinear, or substantially parallel. Alternately, the flexible tip 4 and the anvil 2 may be oriented differently relative to one another. The flexible tip 4 may be tapered distally. That is, the flexible tip 4 may be narrower at its distal end than at its proximal end. The flexible tip 4 may be generally conical. However, the flexible tip 4 may be shaped differently, in any suitable manner.

Referring to FIGS. 2-3, one example of a flexible tip 4 is shown. A segment of wire 6 is spirally wound about the centerline of the flexible tip 4, forming a coil 8. The wire 6 may be radially symmetrical about the longitudinal centerline of the flexible tip 4, may be bilaterally symmetrical about the longitudinal centerline of the flexible tip 4, or may be at least partially asymmetrical about the longitudinal centerline of the flexible tip 4. The wire 6 may be metallic or nonmetallic. As one example, the wire 6 is stainless steel. Adjacent windings of the coil 8 may be substantially in contact with one another, or spaced apart from one another. The cross-section of the wire 6 may be generally circular, or shaped in another manner. The cross-section of the wire 6 may be constant, or may vary, along the length of the wire 6. Optionally, the coil 8 may be welded longitudinally across two or more adjacent windings of wire 6, in order to increase rigidity of the flexible tip 4 and/or to prevent the buckling of one winding over its proximal neighbor during compressive loading. Such weld lines may be repeated at various intervals along the circumference and/or length of the flexible tip 4, and may be of similar or different longitudinal lengths.

A central core 10 may extend substantially along the longitudinal centerline of the coil 8. The central core 10 may be thin and elongated. The central core 10 may be of uniform cross-section, or it may have a tapered cross-section so as to have different elastic properties at different locations along its length. The central core 10 may be a wire, rod, or any other suitable structure. The central core 10 may be metallic or nonmetallic. As one example, the central core 10 is stainless steel. The distal end of the central core 10 may be fixed to a cap 12 having a width at least as great as the distal end of the coil 8. The cap 12 and central core 10 may be fabricated as an integral unit, or may be two separate components that are assembled together. The cap 12 may be placed distal to and in contact with the distal end of the coil 8. The distal end of the cap 12 may be blunt. For example, the cap 12 may be shaped as a hemisphere, where the rounded portion of that hemisphere is oriented distally. The central core 10 may be attached to the coil 8 in any suitable manner, such as by welding, by adhesive, by pressure fitting, or by any other suitable mechanism, structure or method. Alternately, the cap 12 may apply compressive force to the coil 8, without being affirmatively attached to the distal end of the coil 8. The proximal end of the central core 10 may be fixed to the anvil 2. Alternately, the proximal end of the central core 10 may extend completely through the anvil 2, and/or be movable relative to the anvil 2. Alternately, the central core 10 may be omitted. The coil 8 may be connected to the anvil 2 in any suitable manner. As one example, referring also to FIG. 5, a tang 18 may extend distally from the anvil 2, and the coil 8 may stretch over the tang 18 and remain held in place on the tang 18 as a result of compressive force acting on the tang 18 by the coil 8. As another example, the coil 8 may be connected to the anvil through the use of a laser weld, adhesive, or other mechanical fastening method. As another example, the coil 8 may not be connected directly to the anvil 2; the distal end of the coil 8 may be connected to the distal end of the central core 10, such that the central core 10 compressively holds the proximal end of the coil 8 in contact with the anvil 2.

Referring to FIG. 4, another example of a flexible tip 4 is shown. This exemplary flexible tip 4 is similar to that disclosed above, but differs in that the central core 10 is not fixed to the cap 12. Instead, the cap 12 includes an aperture 14 therethrough through which the distal end of the central core 10 can extend and retract. That is, the distal end of the central core 10 is selectively extendable beyond the distal end of the flexible tip 4. The distal end 16 of the central core 10 is sharp, such that it can penetrate tissue when it has been extended distally from the cap 12, and be retracted safely out of the way after such tissue penetration has occurred. The distal end 16 of the central core 10 may be sharp simply as a consequence of having a small diameter, or may be sharpened to a point or any other suitable shape. The central core 10 may be extended distally and retracted proximally relative to the cap 12 in any suitable manner. As one example, the central core 10 may extend through the anvil 2 to a handle (not shown), which directly actuates the central core 10 to move distally and proximally relative to the cap 12. As another example, the handle may actuate a control wire, rod, gear, or other mechanism that is connected to the central core 10 and thereby causes the central core 10 to move. Optionally, the cap 12 may be omitted; such that the central core 10 moves through and is guided by the distal end of the coil 8.

Figure 4A:
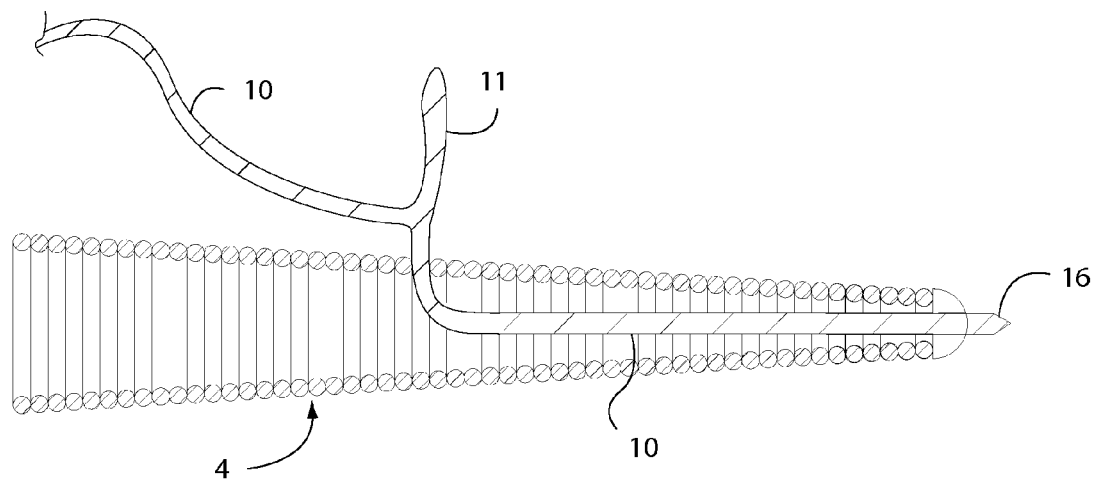
FIG. 4A is a cross-section view of the flexible tip of FIG. 4, including a tissue stop.

Referring also to FIG. 4A, optionally the central core 10 may exit the flexible tip 4 other than through the proximal end of the flexible tip 4, at a location proximal to the distal end of the flexible tip 4. The central core 10 may exit the flexible tip 4 through an aperture in the flexible tip 4, through a location between adjacent coils 8 of the flexible tip 4, or in any other suitable manner. The exit of the central core 10 through the flexible tip 4 other than through the proximal end of the flexible tip 4 may be referred to as an outer surface exit of the central core 10. Outside of the flexible tip 4, the central core 10 may be connected to or may form a tissue stop 11. The tissue stop 11 extends outward from the flexible tip 4 any suitable distance, and acts to stop the motion of the flexible tip 4 into a blood vessel or other tissue, as described in greater detail below. The tissue stop 11 may be generally finger-like and generally blunt, or may be shaped in any other suitable manner. The tissue stop 11 may extend generally perpendicular to the longitudinal centerline of the flexible tip 4, or may be oriented in any other suitable manner. Optionally, the central core 10 may extend proximal to the tissue stop 11. If so, the portion of the central core 10 extending proximally to the tissue stop 11 may re-enter the anvil 2 or a portion of a tool to which the anvil 2 is attached. Alternately, the portion of the central core 10 extending proximally to the tissue stop 11 remains outside the anvil 2 and/or a portion of a tool to which the anvil 2 is attached.

Figure 5:
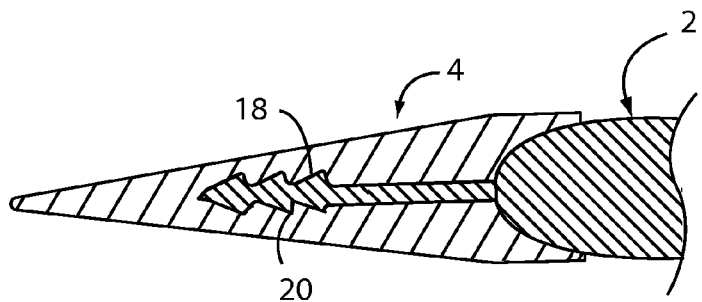
FIG. 5 is a cross-section view of another example of a flexible tip.

Referring to FIG. 5, another example of a flexible tip 4 is shown. The flexible tip 4 is a substantially solid volume of a flexible substance, such as a thermoplastic elastomer (TPE), silicone, rubber or any other suitable material. The flexible substance is molded onto, or otherwise connected to, a tang 18 that extends distally from the anvil 2. Alternately, the flexible substance may be attached to the tang 18 in any other suitable manner, such as by adhesive, or by shrink-fitting. Alternately, the tang 18 may be omitted, and the flexible substance is molded directly onto or otherwise connected directly to the anvil 2. The tang 18 may be shaped in any way that facilitates connection between it and the flexible substance. As one example, the tang 18 may include small projections 20 therefrom and/or apertures therethrough. The flexible tip 4 may be fabricated to have any suitable shape. As one example, the flexible tip 4 may be tapered distally, and may be generally conical.

Operation

In this section of the document, treatment of a blood vessel is described. However, the anvil 2 and flexible tip 4 are not limited to use in treating a blood vessel; any other suitable tissue within a patient may be treated. Referring to the flexible tip of FIGS. 2-3 and 5, a blood vessel of a patient, such as a coronary artery, is incised with a scalpel, needle or other suitable surgical tool. The resulting incision may be round, linear or otherwise shaped, and may be as small as feasible. Next, the anvil 2 and flexible tip 4 are advanced toward the incision. The cap 12 and the distal end of the flexible tip 4 are inserted into the incision. Because the flexible tip 4 is tapered, it can enter the incision easily even if the incision is small. The flexible tip 4 is then advanced into the lumen of the blood vessel through the incision. This motion of the flexible tip 4 may expand the incision if the incision is narrower than a part of the flexible tip 4. Alternately, all points along the flexible tip 4 are narrower than the incision, such that the flexible tip 4 does not expand the incision during insertion. The flexible tip 4 continues to advance into the lumen of the blood vessel as the anvil 2 enters the lumen of the blood vessel through the incision, and at least part of the anvil 2 moves into a final position within the blood vessel, such as a position at an anastomosis site. The anvil 2 may be connected to a connector holder or other mechanism or structure that holds at least one connector, where the connector holder and/or connectors are positioned outside the target vessel when at least part of the anvil 2 is positioned inside the target vessel. At least one connector then may be deformed against the anvil 2 from outside the wall of the blood vessel, such as to connect a graft to the blood vessel. Advantageously, no connector is deployed against the flexible tip 4. However, the flexible tip 4 may be configured to allow at least one connector to be deployed against it. The anvil 2 and flexible tip 4 are then removed from the incision, which may be closed in any suitable manner, or which may naturally close on its own.

Referring to the flexible tip 4 of FIG. 4, the incision in the target vessel is made by the flexible tip 4 itself. The distal end of the central core 10 is initially positioned outside and distal to the cap 12. Alternately, the distal end of the central core 10 is initially positioned inside the coil 8, proximal to the cap 12, and is then extended to a location outside and distal to the cap 12. The anvil 2 is moved toward the blood vessel, and an incision is created in the wall of the blood vessel by penetrating the distal end of the central core 10 through the wall of the blood vessel. The distal end of the flexible tip 4 is advanced slightly into the incision. Where the flexible tip 4 of FIG. 4A is used, the distal end of the flexible tip is advanced into the incision until the tissue stop 11 encounters an edge of that incision. The tissue stop 11 is substantially flat and/or blunt, and extends outward from the flexible tip 4 to increase the effective cross-section of the flexible tip 4. As a result, the flexible tip 4 cannot substantially move further into the incision after the tissue stop 11 encounters the edge of the incision. Because the tissue stop 11 is blunt, it does not substantially expand the size of the incision upon encountering the incision. Contact between the tissue stop 11, which is too large to fit through the incision, and the edge of the incision causes the advancement of the flexible tip 4 to stop. The distance between the distal end of the flexible tip 4 and the tissue stop 11 substantially determines how much of the flexible tip 11 is allowed into the lumen of the blood vessel. The central core 10 is then retracted proximally into the coil 8, such that the distal end of the central core 10 is no longer exposed. In this way, the back wall of the blood vessel is protected as the flexible tip 4 is then advanced into the lumen of the blood vessel, followed by at least a portion of the anvil 2. Optionally, blood may flow through the cap 12 or the distal end of the coil 8, and then laterally out of the coil 8, which may provide visual feedback that the blood vessel has indeed been punctured. At least part of the anvil 2 moves into a final position within the blood vessel, such as a position at an anastomosis site. At least one connector then may be deformed against the anvil 2 from outside the wall of the blood vessel, such as to connect a graft to the blood vessel. Advantageously, no connector is deployed against the flexible tip 4. However, the flexible tip 4 may be configured to allow at least one connector to be deployed against it. The anvil 2 and flexible tip 4 are then removed from the incision, which may be closed in any suitable manner, or which may naturally close on its own.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical method for treating a tissue structure having a wall and a lumen, the method comprising:
   providing a surgical device having a substantially rigid anvil and a flexible tip affixed to and extending from a distal end of said anvil, wherein the flexible tip comprises a length of spirally-wound wire;
   making an incision in the wall of the tissue structure;
   inserting said flexible tip and at least a portion of said rigid anvil through the incision into the lumen of the tissue structure; and
   deforming at least one connector, introduced from outside the wall of the tissue structure, against said portion of said rigid anvil that is located within the lumen of the tissue structure, to apply said at least one connector to the tissue structure.

2. The surgical method of claim 1, wherein said flexible tip includes a central core extendable therefrom and retractable thereinto, and wherein making the incision comprises:
   extending a distal end of said central core from said flexible tip; and
   penetrating the distal end of said central core completely through the wall of the tissue structure.

3. The surgical method of claim 2, wherein extending the distal end of said central core comprises extending said central core through an outer surface of said flexible tip, and wherein inserting said flexible tip comprises inserting said tip until a tissue stop attached to said central core outside of said flexible tip encounters an edge of the incision.

4. The surgical method of claim 1, wherein making the incision comprises using said flexible tip to make the incision.

5. The surgical method of claim 1, further comprising enlarging the incision by inserting said flexible tip through the incision.

6. The surgical method of claim 1, wherein the tissue structure comprises a blood vessel, and wherein deforming said at least one connector connects a graft to a wall of the blood vessel.

7. A surgical method for applying staples to a tissue structure having a wall and a lumen, the method comprising:
   providing a surgical stapler having a substantially rigid anvil, a flexible tip affixed to and extending from a distal end of said anvil, wherein said flexible tip comprises a length of spirally-wound wire, a staple holder associated with said anvil, and a plurality of staples held by said staple holder;
   making an incision in the wall of the tissue structure;
   inserting said flexible tip and at least a portion of said rigid anvil through the incision into the lumen of the tissue structure;
   maintaining said staple holder outside the lumen and the wall of the tissue structure;
   urging at least some of said plurality of staples from said staple holder toward the wall of the tissue structure and said anvil; and
   deforming said urged staples, introduced from outside the wall of the tissue structure, against said portion of said rigid anvil that is located within the lumen of the tissue structure, to apply said urged staples to the tissue structure.

8. The surgical method of claim 7, wherein the tissue structure comprises a blood vessel, and wherein deforming said urged staples connects a graft to a wall of the blood vessel.

* * * * *